United States Patent
Jansen et al.

(10) Patent No.: US 9,931,285 B2
(45) Date of Patent: *Apr. 3, 2018

(54) MULTI-STEP PRODUCT FOR IMPROVING THE APPEARANCE AND FEEL OF HUMAN SKIN

(71) Applicant: The Procter & Gamble Company, Cincinnati, OH (US)

(72) Inventors: Joseph Harry Jansen, Harrison, OH (US); Joseph Michael Zukowski, Cincinnati, OH (US); Paul Robert Tanner, Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/596,363

(22) Filed: Jan. 14, 2015

(65) Prior Publication Data

US 2015/0196471 A1    Jul. 16, 2015

Related U.S. Application Data

(60) Provisional application No. 61/927,236, filed on Jan. 14, 2014.

(51) Int. Cl.
| | |
|---|---|
| *A61K 8/34* | (2006.01) |
| *A61Q 19/00* | (2006.01) |
| *A61Q 19/08* | (2006.01) |
| *A61Q 19/02* | (2006.01) |
| *A61Q 5/12* | (2006.01) |
| *A61K 8/25* | (2006.01) |
| *A61K 8/29* | (2006.01) |
| *A61K 8/19* | (2006.01) |
| *A61Q 1/12* | (2006.01) |
| *A61K 8/73* | (2006.01) |
| *A61K 8/02* | (2006.01) |

(52) U.S. Cl.
CPC .............. *A61K 8/345* (2013.01); *A61K 8/025* (2013.01); *A61K 8/19* (2013.01); *A61K 8/25* (2013.01); *A61K 8/29* (2013.01); *A61K 8/732* (2013.01); *A61Q 1/12* (2013.01); *A61Q 5/12* (2013.01); *A61Q 19/007* (2013.01); *A61Q 19/02* (2013.01); *A61Q 19/08* (2013.01); *A61K 2800/884* (2013.01)

(58) Field of Classification Search
None
See application file for complete search history.

(56) References Cited

U.S. PATENT DOCUMENTS

| | | |
|---|---|---|
| 3,755,560 A | 8/1973 | Dickert |
| 4,421,769 A | 12/1983 | Dixon |
| 5,041,281 A | 8/1991 | Strobridge |
| 5,223,559 A | 6/1993 | Arraudeau |
| 5,871,761 A | 2/1999 | Kuwata et al. |
| 5,871,791 A | 2/1999 | Noble |
| 6,367,484 B1 | 4/2002 | Ramin |
| 6,531,116 B1 | 3/2003 | Utecht |
| 6,780,422 B2 | 8/2004 | Brieva et al. |
| 6,872,401 B2 | 3/2005 | Seyler |
| 7,172,754 B1 | 2/2007 | Rosevear et al. |
| 7,351,417 B2 | 4/2008 | Barrow et al. |
| 8,425,884 B2 | 4/2013 | Takakura et al. |
| 2002/0193513 A1 | 12/2002 | Bara |
| 2003/0031642 A1 | 2/2003 | Lezer |
| 2003/0049212 A1 | 3/2003 | Robinson |
| 2003/0095941 A1 | 5/2003 | Anderson |
| 2004/0086473 A1 | 5/2004 | Rabe |
| 2004/0086474 A1 | 5/2004 | Rabe |
| 2004/0228819 A1 | 11/2004 | Rabe |
| 2005/0058677 A1 | 3/2005 | Ricard |
| 2005/0058678 A1 | 3/2005 | Ricard |
| 2006/0057127 A1 | 3/2006 | Liu |
| 2006/0057217 A1 | 3/2006 | Utschig |

(Continued)

FOREIGN PATENT DOCUMENTS

| | | |
|---|---|---|
| DE | 10157490 | 6/2003 |
| EP | 0502769 A1 | 9/1992 |

(Continued)

OTHER PUBLICATIONS

Todd, Charles et al. "Volatile Silicone Fluids for Cosmetic Formulations", 91 Cosmetics and Toiletries 27-32 (1976).
"The CIE 1976 Color Difference Formulas," *Color Research Applications*, vol. 2, pp. 7-11 (1977).
International Search Report PCT/US2015/011366; dated Apr. 30, 2015; 22 pages.
International Search Report PCT/US2015/011367; dated Apr. 30, 2015; 22 pages.
International Search Report PCT/US2015/011370; dated Apr. 30, 2015; 21 pages.

(Continued)

*Primary Examiner* — Ernst V Arnold
*Assistant Examiner* — Kyung Sook Chang
(74) *Attorney, Agent, or Firm* — John G. Powell; S. Robert Chuey

(57) ABSTRACT

A multi-layer product for improving the look of human skin by the steps of: apply to the skin a first layer that is a skin care composition; and applying to, and on top of, the first layer, a powder layer. The powder layer has from about 10% to about 30%, by weight of the powder layer, of substantially spherical particles selected from the group consisting of coated or uncoated starch, silicone elastomer particles, and combinations thereof. The powder layer is an aqueous based composition that is an oil-in-water emulsion comprising a non-volatile oil present in a concentration level such that the weight ratio of non-volatile oil to particulate material is from about 1:10 to about 3:2. At least one of, or both the first layer and the powder layer have a contrast ratio of less than about 20.

11 Claims, 1 Drawing Sheet

(56) References Cited

U.S. PATENT DOCUMENTS

| | | |
|---|---|---|
| 2006/0257346 A1 | 11/2006 | Mohammadi |
| 2007/0059262 A1 | 3/2007 | Taniguchi |
| 2007/0065381 A1* | 3/2007 | Elsbrock .............. A61K 8/11 424/63 |
| 2007/0224141 A1 | 9/2007 | Themens |
| 2007/0237730 A1 | 10/2007 | Polonka |
| 2008/0145435 A1 | 6/2008 | Ricard |
| 2008/0181956 A1 | 7/2008 | Ha |
| 2009/0148393 A1 | 6/2009 | Maitra et al. |
| 2009/0208443 A1 | 8/2009 | Polonka |
| 2010/0266651 A1 | 10/2010 | Czech et al. |
| 2010/0322983 A1 | 12/2010 | Griffiths-Brophy |
| 2013/0095324 A1 | 4/2013 | Inokuchi |
| 2013/0243835 A1 | 9/2013 | Tanner et al. |
| 2014/0341823 A1 | 11/2014 | Alard |
| 2016/0346189 A1 | 12/2016 | Jansen et al. |

FOREIGN PATENT DOCUMENTS

| | | |
|---|---|---|
| EP | 1513491 B1 | 3/2005 |
| EP | 1767191 A1 | 3/2007 |
| EP | 2382961 A2 | 11/2011 |
| EP | 1902704 B1 | 11/2013 |
| EP | 2823807 A1 | 1/2015 |
| FR | 2964562 B1 | 3/2012 |
| FR | 2903306 B1 | 6/2012 |
| GB | 2423250 A | 8/2006 |
| JP | H1059817 A | 3/1998 |
| JP | H11158036 A | 6/1999 |
| JP | 2003055134 A | 2/2003 |
| JP | 2003238356 A | 8/2003 |
| JP | 2003300831 | 10/2003 |
| JP | 2005200407 A | 7/2005 |
| JP | 2007269690 A | 10/2007 |
| WO | WO2002/092047 | 11/2002 |
| WO | WO2012168102 A2 | 12/2012 |
| WO | WO2013/088046 | 6/2013 |
| WO | WO2013/166342 | 11/2013 |
| WO | WO2013/169506 | 11/2013 |

OTHER PUBLICATIONS

International Search Report PCT/US2015/011372; dated Apr. 30, 2015; 22 pages.
"Prime & Anti-Shine Balm" GNPD Nov. 1, 2013; Record ID 2247832.
All Office Actions, U.S. Appl. No. 14/245,230.
All Office Actions, U.S. Appl. No. 14/245,241.
All Office Actions, U.S. Appl. No. 14/445,434.
All Office Actions, U.S. Appl. No. 14/445,456.
All Office Actions, U.S. Appl. No. 14/596,360.
All Office Actions, U.S. Appl. No. 14/596,374.
All Office Actions, U.S. Appl. No. 14/596,379.
Dow Corning DC 9506 Powder product information(date: Jul. 24, 2003).
International Search Report and Written Opinion of the International Searching Authority, PCT/US2015/011373, dated Apr. 14, 2015, 10 pages.
International Search Report and Written Opinion of the International Searching Authority, PCT/US2015/011374, dated Apr. 17, 2015, 11 pages.
International Search Report and Written Opinion of the International Searching Authority, PCT/US2015/041884, dated Sep. 16, 2015, 11 pages.
International Search Report and Written Opinion of the International Searching Authority, PCT/US2015/041886, dated Oct. 2, 2015, 10 pages.
Koboguard 5400 IDD published Jun. 2005 (2 pages).
Roussel et al., Glycerol as a skin barrier influencing humectant, Treatment of Dry Skin Syndrome, Chapter 32, pp. 473-480, 2012.

* cited by examiner

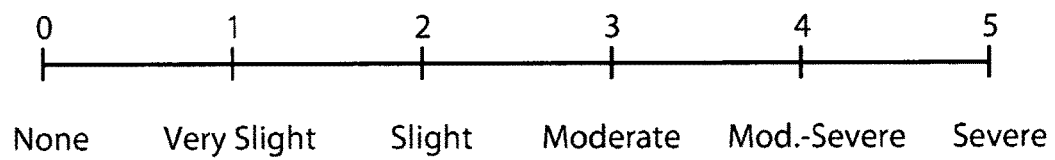

MULTI-STEP PRODUCT FOR IMPROVING THE APPEARANCE AND FEEL OF HUMAN SKIN

FIELD OF THE INVENTION

The present invention relates to a multi-step product for improving the appearance and feel of human skin. The product comprises applying an oil in water emulsion containing a high concentration of powder on top of a skin care composition that is applied first to the human skin.

BACKGROUND OF THE INVENTION

Personal care products are well known and widely used. These products have long been employed to cleanse and moisturize, deliver actives, hide imperfections and to reduce the oiliness and shine on keratinous surfaces. Personal care products have also been used to alter the color and appearance of skin and hair. A variety of personal-care compositions are available to provide skin care benefits and to counteract what many consider undesirable "signs of skin aging," such as fine lines, wrinkles, and uneven skin texture. Of these benefits, the look and feel of human skin are arguably the two most important and desired effects by consumers.

Many products are designed to improve the look of human skin and many products are directed to improving the feel. Traditionally, a wide variety of different functional materials are combined in a single skin care product in an attempt to deliver a range of benefits to consumers. For example, a typical skin care product might contain: humectants and other skin actives to improve the condition and health of the skin; emollients to lubricate the skin; and a wide variety of powders to provide a skin feel and immediate skin appearance benefit. But combining compositions into one product often has difficulties.

Moreover, products that deliver one benefit are generally intended as a single application product. Layering many products on the skin that deliver different benefits, but are intended to be used individually, may have the same drawbacks and complications as mixing too many ingredients in one composition. Hence there is a need for products and regimens that deliver multiple benefits, in different compositions, but are designed to be used together in a coordinated regimen.

For example, particulate material can be added to consumer products for a variety of reasons such as to improve the skin feel of the product. Particulate materials also may provide an immediate visible benefit to the skin by diffusely reflecting light, which provides a matting effect to the skin. However, many particulate materials are added to act as an opacifying agent, which effectively turns the consumer product into make-up or make-up like product. The acute and chronic benefits of personal care compositions having opacifying agents are often lost on the user who only appreciates the masking effect the opacifying agents provide. Examples of these include high refractive index pigments, such as titanium dioxide and iron oxides, to provide skin color benefits.

Micronized or spherical polymer particles are used to provide feel and visible texture, wrinkle reduction benefits. For these materials, however, there are tradeoffs if one attempts to increase these feel and look benefits. Using high levels of powder typically lead to products that are hard to spread on skin, and that lose their look benefits over time. These products typically become noticeably white and can flake off the skin.

Likewise, humectants provide a multitude of skin health and appearance benefits, such as: increasing skin translucency, as evidenced by less surface scattering and reducing refractive index gradients in the stratum corneum; reducing visible texture, that is, plumping of the stratum corneum; and generally better functioning and stronger skin. Glycerin is the most efficient humectant available due to its chemical structure. But glycerin is a very thick, sticky material and high levels of glycerin can feel very sticky and heavy on the skin. Moreover, high levels of glycerin on the skin can make it look very shiny and greasy, given that glycerin is slow to absorb into the skin.

Therefore, a need exists for personal care compositions with a high percentage of a particulate material having a low refractive index that can be applied on top of one or more personal care compositions that contain high levels of humectants. This layering effect avoids the drawbacks of combining an "all-in-one" composition, and the drawbacks of layering products not designed to be used together. That is, separating a product in a specific way into two or more layers and applying those layers to skin in a specific sequence, skin feel and skin appearance benefits can be greatly enhanced. More specifically, there exists a need for a regimen and multi layer products comprising an aqueous layer with the product's humectants and skin actives first, and an aqueous layer containing the product's powders last.

SUMMARY OF THE INVENTION

There is provided a multi-step product for improving the look of human skin comprising: applying to the skin a first layer that is a skin care composition containing glycerin; and applying to, and on top of, the first layer, a powder layer. The first layer comprises from about 8%, preferably from about 12%, and even more preferably from about 15% to about 30%, preferably to about 25%, more preferably to about 20%, by weight of the first layer, of glycerin. The powder layer contains from about 10%, preferably from about 12%, even more preferably from about 15%, to about 30%, preferably to about 25%, by weight of the powder layer, of substantially spherical particles. The particles may be selected from the group consisting of coated starch, uncoated starch, silicone elastomer particles, and combinations thereof. Preferably the particles are selected from the group consisting of tapioca starch, corn starch, potato starch, glyceryl starch, aluminum starch octenylsuccinate, calcium starch octenylsuccinate, and polymethylsilsesquioxane coated tapioca starch, cross linked starch, silicone elastomer particles, and combinations thereof.

Further, the powder layer is an aqueous based composition that is an oil-in-water emulsion comprising a non-volatile oil present in a concentration level such that the weight ratio of non-volatile oil to particulate material is from about 1:10 to about 3:2, preferably from about 1:4 to about 1:1, and more preferably from about 1:4 to about 3:4. At least one of, or both the first layer and the powder layer each have a contrast ratio of less than about 20, preferably less than about 10 and even more preferably less than about 6. The first layer comprises from about 2%, preferably from about 5%, preferably from about 10% to about 25%, more preferably to about 20% by weight of the first layer, other humectants. Further provided are methods to accomplish the multi-step regimens of the present invention.

The methods, regimens and compositions of the present invention overcome many issues of prior personal care compositions and regimens. By placing different skin care components in different compositions and then applying them in a particular order in a multi step process, the sticky, heavy feel of the humectants is greatly reduced, the smooth, powdery feel of the powders is enhanced, and the appearance benefits from the powders is significantly increased.

BRIEF DESCRIPTION OF THE DRAWING

The FIGURE shows a 5-point continuous line scale for grading skin features.

DETAILED DESCRIPTION

The personal care product of the present invention may be used in skin care and cosmetics, non-limiting uses of which include moisturizers, conditioners, anti-aging compounds, skin lightening compounds, and combinations thereof. The composition is applied to keratinous tissue of the face, neck, hands, arms and other areas of the body.

Percentages are by weight of the personal care composition or the particular phase being described, unless otherwise specified. All ratios are weight ratios, unless specifically stated otherwise. All numeric ranges are inclusive of narrower ranges. The number of significant digits conveys neither limitation on the indicated amounts nor on the accuracy of the measurements. All measurements are understood to be made at ambient conditions, where "ambient conditions" means conditions at about 25° C., under about one atmosphere of pressure, and at about 50% relative humidity.

"Personal care product" means a product with a composition suitable for topical application on mammalian keratinous tissue.

"Keratinous tissue" refers to keratin-containing layers disposed as the outermost protective covering of mammals which includes, but is not limited to, skin, hair, nails, cuticles, etc.

"Derivative" refers to a molecule similar to that of another one, but differing from it in respect of a certain functional moiety. Derivatives may be formed by known reactive pathways. Suitable functional moieties include esters, ethers, amides, amines, carboxylic acids, hydroxyls, halogens, thiols, and/or salt derivatives of the relevant molecule.

"Substituted" means comprising at least one heteroatomic substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups.

"Apply" or "application," as used in reference to a composition, means to apply or spread the composition onto a keratinous tissue surface.

"Substantially free of" as used herein, means that the composition comprises less than about 3%, preferably less than about 1%, more preferably less than about 0.5%, even more preferably less than about 0.25%, and most preferably less than about 0.1%, by weight of the composition, of the stated ingredient.

"Regulating skin condition" means improving skin appearance and/or feel, for example, by providing a benefit, such as a smoother appearance and/or feel. Herein, "improving skin condition" means effecting a visually and/or tactilely perceptible positive change in skin appearance and feel. The benefit may be a chronic or acute benefit and may include one or more of the following: reducing the appearance of wrinkles and coarse deep lines, fine lines, crevices, humps, and large pores; thickening of keratinous tissue (e.g., building the epidermis and/or dermis and/or sub-dermal layers of the skin, and where applicable the keratinous layers of the nail and hair shaft, to reduce skin, hair, or nail atrophy); increasing the convolution of the dermal-epidermal border (also known as the rete ridges); preventing loss of skin or hair elasticity, for example, due to loss, damage and/or inactivation of functional skin elastin, resulting in such conditions as elastosis, sagging, loss of skin or hair recoil from deformation; reduction in cellulite; change in coloration to the skin, hair, or nails, for example, under-eye circles, blotchiness (e.g., uneven red coloration due to, for example, rosacea), sallowness, discoloration caused by hyperpigmentation, etc.

"Signs of skin aging," include, but are not limited to, all outward visibly and tactilely perceptible manifestations, as well as any macro- or micro-effects, due to keratinous tissue aging. These signs may result from processes which include, but are not limited to, the development of textural discontinuities such as wrinkles and coarse deep wrinkles, fine lines, skin lines, crevices, bumps, large pores, unevenness or roughness; loss of skin elasticity; discoloration (including undereye circles); blotchiness; sallowness; hyperpigmented skin regions such as age spots and freckles; keratoses; abnormal differentiation; hyperkeratinization; elastosis; collagen breakdown, and other histological changes in the stratum corneum, dermis, epidermis, vascular system (e.g., telangiectasia or spider vessels), and underlying tissues (e.g., fat and/or muscle), especially those proximate to the skin.

"Non-volatile" means a material that exhibit a vapor pressure of no more than about 0.2 mm Hg at 25° C. at one atmosphere and/or a material that has a boiling point at one atmosphere of at least about 300° C. "Volatile" means that the material exhibits a vapor pressure of at least about 0.2 mm of mercury at 20° C.

"Safe and effective amount" means an amount of a compound or composition sufficient to induce a positive benefit but low enough to avoid serious side effects (i.e., provides a reasonable benefit to risk ratio within the judgment of a skilled artisan).

Personal-Care Compositions for Use in a Multi-Step Regimen

The personal-care compositions of the present invention may be skin care or cosmetic products. The personal-care compositions may be used as, for example, a moisturizer, conditioner, anti-aging compound, or skin-lightening compound. In certain embodiments, the composition is applied to the face, neck, hands, arms, and other typically exposed areas of the body.

The compositions of the present invention are useful for improving skin appearance and feel. The compositions of the present invention may be useful for regulating skin condition and improving skin condition. In certain embodiments, the composition is useful for regulating and improving the signs of skin aging. The compositions may provide an essentially immediate (i.e., acute) improvement in skin appearance and feel following application. It is believed that the acute improvement may be attained with a single or limited number of applications of the composition. However, the compositions may comprise components that provide a gradual (i.e., chronic) improvement in skin appearance and feel. It is believed that the chronic improvement may involve multiple, reoccurring, or periodic applications of the composition. The compositions of the present invention may be incorporated into consumer products. In certain embodiments, the consumer products allow the composition to be applied as a spot treatment over a limited area of the skin. In one embodiment, the compositions of the present invention yield a visibly noticeable reduction in wrinkles or bumps on the skin.

The first layer of the present compositions can be any skin care composition, non-limiting examples include, liquids, creams and lotions. Preferably, the first layer is water based, more preferably, a water continuous formation. More specifically, the first layer compositions of the present invention can be in the form of an aqueous solution, aqueous gel, aqueous dispersion, oil-in-water emulsion, or a water-in-oil-in-water emulsion. While the powder layer is preferably an oil-in-water emulsion. The oil phase of the present invention, when present, may comprise a silicone oil. However, the oil phase may also comprise non-silicone oils such as hydrocarbon oils, esters, ethers, and the like.

The aqueous phase of either the first layer or the powder layer typically comprises water. The first layer may comprise about 20% to about 99%, preferably about 40% to about 90%, and more preferably from about 50% to about 85%, of water. The powder layer may comprise about 20% to about 85%, preferably about 30% to about 80%, and more preferably from about 40% to about 75%, of water. The aqueous phase of either the first layer or the powder layer may comprise components other than water (non-water components), including but not limited to water-soluble moisturizing agents, conditioning agents, anti-microbials, humectants and other water-soluble skin care actives, to impart an increased benefit to the keratinous tissue.

Methods of Using the Multi-Step Compositions

The present invention describes a method of providing benefits to human skin, specifically, the benefits of simultaneously improving the look and feel of human skin. Even more specifically, the compositions may be applied to skin exhibiting signs of skin aging, for example, to reduce the appearance of wrinkles, which include reducing the appearance of wrinkles, reducing the appearance of deep lines, reducing the appearance of fine lines, reducing the appearance of large pores and bumps on the skin. Further the skin is hydrated and moisturized. The individual ingredients of the compositions of this invention, both required and optional, as well as their properties and concentration levels, are defined in greater detail below.

There is provided herein a multi-step process where the first step is applying a first layer, which is a skin care product. The second step is applying a powder layer, that is, a composition comprising high levels of particulate material. The skin care product is preferably a moisturizing composition, and even more preferably, a composition comprising high levels of humectant. Both the first layer and the powder layers are preferably aqueous based. The powder layer contains non-volatile oils in specific ratios with respect to the particulate concentration.

The layers of the present compositions are kept separate until use to insure they can be applied in the proper order, which, as the comparative examples will illustrate, is an important aspect of the present invention. The compositions can, however, be sold in a variety of ways. The multiple layers can be sold in the same package, if separated until dispensed. The compositions can be sold in individual containers that are sold separately or together. Non-limiting examples include one box that contains multiple bottles, each bottle containing a different layer, or the layers can be sold separately in an array of packages where the consumer can select from various different versions of each layer.

The compositions may be applied by a variety of means, including by rubbing, wiping or dabbing with hands or fingers, or by means of an implement and/or delivery enhancement device. Non-limiting examples of implements include a sponge or sponge-tipped applicator, a swab (for example, a cotton-tipped swab), a pen optionally comprising a foam or sponge applicator, a brush, a wipe, and combinations thereof. Non-limiting examples of delivery enhancement devices include mechanical, electrical, ultrasonic and/or other energy devices. After application, the composition may be allowed to remain on the skin.

The amount of the composition applied, the frequency of application and the period of use will vary widely depending upon the level of components of a given composition and the level of regulation desired. For example, from about 0.1 mg composition/cm$^2$ to about 50 mg composition/cm$^2$, and alternatively about 2 mg composition/cm$^2$ of skin may be applied. In one embodiment, the composition is applied at least once daily, where "daily" and "days" mean a 24-hour period. The user may be instructed to reapply the composition after a period of time has passed, for example every hour, and alternatively when the composition has been washed or rinsed from the skin, for example after washing one's hands or face, or after swimming, bathing and showering. The compositions may be applied as part of a treatment regimen, for example, once daily for 30 consecutive days, alternatively for 14 consecutive days, alternatively for 7 consecutive days and alternatively for 2 consecutive days.

Ingredients

Humectant

The first layer of the present invention includes glycerin and may include one or more additional humectants. Preferably the powder layer has less than about 10% humectant, preferably less than about 5% humectant, and more preferably the powder layer is substantially free of humectant. The first layer of the present invention may comprise about 8%, preferably from about 12%, and even more preferably from about 15% to about 30%, preferably to about 25%, more preferably to about 20%, by weight of the first layer, of glycerin. The first layer may optionally comprise from about 2%, preferably from about 5%, preferably from about 10% to about 25%, more preferably to about 20% by weight of the first layer, other humectants An exemplary class of humectants is polyhydric alcohols. Suitable polyhydric alcohols include polyalkylene glycols and alkylene polyols and their derivatives, including propylene glycol, dipropylene glycol, polypropylene glycol, polyethylene glycol and derivatives thereof; sorbitol; hydroxypropyl sorbitol; erythritol; threitol; pentaerythritol; xylitol; glucitol; mannitol; butylene glycol (e.g., 1,3-butylene glycol); pentylene glycol; hexane triol (e.g., 1,2,6-hexanetriol); ethoxylated glycerine; and propoxylated glycerine.

Other suitable humectants include sodium 2-pyrrolidone-5-carboxylate, guanidine; glycolic acid and glycolate salts (e.g., ammonium and quaternary alkyl ammonium); lactic acid and lactate salts (e.g., ammonium and quaternary alkyl ammonium); aloe vera in any of its variety of forms (e.g., aloe vera gel); hyaluronic acid and derivatives thereof (e.g., salt derivatives such as sodium hyaluronate); lactamide monoethanolamine; acetamide monoethanolamine; urea; sodium pyroglutamate, water-soluble glyceryl poly(meth) acrylate lubricants (such as Hispagel®) and mixtures thereof.

Particulate Material

The compositions of the present invention comprise particulate materials. The particulate material may be dispersed and suspended in the composition. The particulate material may be used to provide consumer desirable look and feel properties to the compositions. These particles give the composition a silky or lubricious feel which may offset the heavy greasiness associated with oils and/or the tacky feel of many humectants.

The particulate material may exhibit a median particle size of from about 1 µm to about 40 µm; from about 2 µm to about 30 µm; from about 5 µm to about 30 µm; from about 5 µm to about 25 µm; or, alternatively, from about 5 µm to about 20 µm. Median particle size can be determined by any suitable method known in the art, such as by using coulter-counter equipment or the ASTM Designation E20-85 "Standard Practice for Particle Size Analysis of Particulate Substances in the Range of 0.2 to 75 Micrometers by Optical Microscopy," ASTM Volume 14.02, 1993, incorporated herein by reference.

The powder layer of the present invention preferably comprise from about 10% to about 30%, or from about 12% to about 25%, by weight, of the particulate material. The median particle size is measured, and the concentration levels are calculated when the particulate material is in the neat form (i.e., in the essentially pure, powder form prior to combination with the carrier of the invention).

In various embodiments, the particulates are preferably spherical. In the present invention, "spherical" and "sphere" mean not only real sphere but also include deformed sphere wherein major axis/minor axis (aspect ratio) on average is typically in the range of 1 to 4, preferably 1 to 2, more preferably 1 to 1.6, and even more preferably 1 to 1.4. The shape of the fine particles may be confirmed by observing the fine particle with an optical microscope or electron microscope.

Preferably, the powder layer comprises less than about 1%, preferably less than about 0.5%, by weight of the powder layer of $TiO_2$ and iron oxide particles, or other particles that impart color, or chroma, or opacity to the powder layer. Further, the powder layer comprises less than about 4%, preferably less than about 3%, and even more preferably less than about 1%, by weight of the powder layer of mica, talc, interference pigments and other substantially non-spherical particles.

Starch Particles

The starch particles in the present invention are comprised of starch, crosslinked starch, starch derivatives, or mixtures of these, and optionally these particles may be partially or fully coated to modify their surface properties. It is important for these starch particles to remain as discrete particles in the powder layer formulations of the present invention, and hence these starches are generally not subject to high temperatures for any extended period of time.

Examples of commercially available starch particles include tapioca starch (available as Tapioca Pure from AkzoNobel), corn starch (available as Purity 21C from AkzoNobel), potato starch, glyceryl starch (available as Dry-Flo GS from AkzoNobel), aluminum starch octenylsuccinate (available as Mackaderm ASTO-Dry from Rhodia, Inc., and Dry-Flo PC from AkzoNobel), calcium starch octenylsuccinate (available as Skin Flow C from MGP Ingredients, Inc., and Mackaderm CSTO-Dry from Rhodia, Inc.), and polymethylsilsesquioxane coated tapioca starch (available as Dry-Flo TS from AkzoNobel).

Spherical Silicone Elastomer Particles

The particles of the present invention may comprise spherical silicone elastomer particles that may optionally have polyorganosilsesquioxane attached on the surface. The silicone elastomer constituting the spherical silicone elastomer particles preferably have no tackiness and the rubber hardness measured by Durometer A defined in JIS K 6253 is preferably in the range of 10 to 90, more preferably 20 to 80, and even more preferably 25 to 75. When the rubber hardness is less than 5, the resulting silicone particles tend to become agglomerated, and dispersion into primary particles will be difficult with decrease in the dryness. The rubber hardness in excess of 90 will invite loss of soft texture. Silicone elastomer particles suitable for the present invention include silicone resin-coated silicone rubber particles. The spherical silicone elastomer particles in the powder layer have an average diameter of from about 1 µm to about 40 µm, preferably from about 2 µm to about 30 µm, from about 5 µm to about 15 µm.

It is known in the prior art that silicone particles can be prepared from several silicone materials, i.e. organopolysiloxanes, including cured silicone rubbers and poly(organosilsesquioxane) resins. Commercially available silicone particles suitable for use in the present invention include: KSP-100, -101, -102, -103, -104, and -105, all from Shin Etsu; and DC9506, and DC 9701 from Dow Corning.

Non-Volatile Oils

Non-volatile oils are used in the present invention. These oils may be used in any of the compositions, layers of the present invention, but are most preferably used in the powder layer. When used in the powder layer the concentration of oil is tied to the amount of particulate material used, specifically, the ratio of non-volatile oil to particulate material is within the range of from 1:10 to 3:2, preferably, from 1:4 to 1:1 and more preferably from 1:4 to 3:4.

Suitable non-volatile oils include hydrocarbons, esters, amides, ethers, silicones, and mixtures thereof. Suitable non-volatile hydrocarbon oils include straight, branched, or cyclic alkanes and alkenes. The chain length may be selected based on desired functional characteristics such as viscosity. Suitable non-volatile esters include esters with hydrocarbyl chains derived from fatty acids or alcohols (e.g., monoesters, polyhydric alcohol esters, and di- and tri-carboxylic acid esters). The hydrocarbyl radicals of the esters hereof may include or have covalently bonded thereto other compatible functionalities, such as amides and alkoxy moieties (e.g., ethoxy or ether linkages, etc.). Exemplary esters include, but are not limited to, isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, C12-15 alkyl benzoate, butyloctyl salicylate, phenylethyl benzoate, dicaprylyl carbonate, dioctyl malate, dicaprylyl maleate, isononyl isononanoate, propylene glycol dicaprate, diisopropyl adipate, dibutyl adipate, and oleyl adipate. Other suitable esters are further described in the Personal Care Product Council's *International Cosmetic Ingredient Dictionary and Handbook*, Thirteenth Edition, 2010, under the functional category of "Esters."

Suitable non-volatile amides include compounds having an amide functional group while being liquid at 25° C. and insoluble in water. Suitable amides include, but are not limited to, N-acetyl-N-butylaminopropionate, isopropyl N-lauroylsarcosinate, butylphthalimide, isopropylphthalimide, and N,N,-diethyltoluamide. Other suitable amides are disclosed in U.S. Pat. No. 6,872,401.

Suitable non-volatile ethers include saturated and unsaturated fatty ethers of a polyhydric alcohol, and alkoxylated derivatives thereof. Exemplary ethers include, but are not limited to, $C_{4-20}$ alkyl ethers of polypropylene glycols, and di-$C_{8-30}$ alkyl ethers. Suitable examples of these materials include PPG-14 butyl ether, PPG-15 stearyl ether, PPG-11 stearyl ether, dioctyl ether, dodecyl octyl ether, and mixtures thereof.

Suitable non-volatile silicone oils include polysiloxanes. Non-volatile polylsiloxanes may have a viscosity of from about 10 to about 1,000,000 centistokes at 25° C. Such polysiloxanes can be represented by the general chemical formula:

$$R_3SiO[R_2SiO]_xSiR_3$$

wherein R is independently selected from hydrogen or $C_{1-30}$ straight or branched chain, saturated or unsaturated alkyl, phenyl or aryl, trialkylsiloxy; and x is an integer from 0 to about 10,000. In certain embodiments, R is methyl or ethyl. Commercially available polysiloxanes include the polydimethylsiloxanes, which are also known as dimethicones, examples of which include the DM-Fluid series from Shin-Etsu, the Vicasil® series sold by Momentive Performance Materials Inc., and the Dow Corning® 200 series sold by Dow Corning Corporation. Specific examples of suitable polydimethylsiloxanes include Dow Corning® 200 fluids (also sold as Xiameter® PMX-200 Silicone Fluids).

Suitable dimethicones include those represented by the chemical formula:

$$R_3SiO[R_2SiO]_x[RR'SiO]_ySiR_3$$

wherein R and R' are each independently hydrogen or $C_{1-30}$ straight or branched chain, saturated or unsaturated alkyl, aryl, or trialkylsiloxy; and x and y are each integers of 1 to 1,000,000. Examples include alkyl dimethicones wherein at least R' is a fatty alkyl (e.g., $C_{12-22}$). A suitable alkyl dimethicone is cetyl dimethicone, wherein R' is a straight C16 chain and R is methyl, commercially available as 2502Cosmetic Fluid from Dow Corning.

Preferred non-volatile oils include dimethicones (polydimethylsiloxanes), preferably with viscosities of between 10 cst and 1000 cst, more preferably between 15 cst to 400 cst, most preferably between 20 cst and 200 cst. The average chain lengths for these preferred dimethicone materials is from about 12 to about 375 dimethylsiloxane units, more preferably from about 20 to to about 200 dimethylsiloxane units, and most preferably with average chain lengths of from about 27 to about 125 dimethylsiloxane units.

Optional Ingredients

Emulsifier

The compositions may comprise an emulsifier. An emulsifier is particularly suitable when the composition is in the form of an emulsion or if immiscible materials are being combined. The compositions may comprise from about 0.05%, 0.1%, 0.2%, 0.3%, 0.5%, or 1% to about 20%, 10%, 5%, 3%, 2%, or 1% emulsifier. Emulsifiers may be nonionic, anionic or cationic. Non-limiting examples of emulsifiers are disclosed in U.S. Pat. No. 3,755,560, U.S. Pat. No. 4,421,769, and McCutcheon's, *Emulsifiers and Detergents*, 2010 Annual Ed., published by M. C. Publishing Co. Other suitable emulsifiers are further described in the Personal Care Product Council's *International Cosmetic Ingredient Dictionary and Handbook*, Thirteenth Edition, 2006, under the functional category of "Surfactants—Emulsifying Agents."

Suitable emulsifiers include the following classes of ethers and esters: ethers of polyglycols and of fatty alcohols, esters of polyglycols and of fatty acids, ethers of polyglycols and of fatty alcohols which are glycosylated, esters of polyglycols and of fatty acids which are glycosylated, ethers of $C_{12-30}$ alcohols and of glycerol or of polyglycerol, esters of $C_{12-30}$ fatty acids and of glycerol or of polyglycerol, ethers of oxyalkylene-modified $C_{12-30}$ alcohols and of glycerol or polyglycerol, ethers of $C_{12-30}$ fatty alcohols comprising and of sucrose or of glucose, esters of sucrose and of $C_{12-30}$ fatty acids, esters of pentaerythritol and of $C_{12-30}$ fatty acids, esters of sorbitol and/or of sorbitan and of $C_{12-30}$ fatty acids, ethers of sorbitol and/or of sorbitan and of alkoxylated sorbitan, ethers of polyglycols and of cholesterol, esters of $C_{12-30}$ fatty acids and of alkoxylated ethers of sorbitol and/or sorbitan, and combinations thereof.

Silicone emulsifiers may be use in the present compositions. Linear or branched type silicone emulsifiers may also be used. Particularly useful silicone emulsifiers include polyether modified silicones such as KF-6011, KF-6012, KF-6013, KF-6015, KF-6015, KF-6017, KF-6043, KF-6028, and KF-6038 and polyglycerolated linear or branched siloxane emulsifiers such as KF-6100, KF-6104, and KF-6105; all from Shin Etsu.

Volatile Oils

The compositions of the present invention may comprise from about 0% to about 30%, or, alternatively, from about 5% to about 20% of one or more volatile oils. Suitable volatile oils include volatile silicones and volatile hydrocarbon oils.

Suitable volatile silicones include cyclic and linear volatile silicones. A description of various volatile silicones is found in Todd, et al. "Volatile Silicone Fluids for Cosmetics", 91 Cosmetics and Toiletries 27-32 (1976). Suitable cyclic volatile silicones include cyclic dimethyl siloxane chains containing an average of from about 3 to about 5 silicon atoms, preferably from about 4 to about 5 silicon atoms. Exemplary cyclic volatile silicones of varying viscosities include Dow Corning DC 244, DC 245, DC 344, and DC 345; GE Silicones-OSi Specialties Volatile Silicone 7207 and Volatile Silicone 7158; and GE Silicones SF1202. Suitable volatile linear silicones include the polydimethylsiloxanes containing an average of from about 2 to about 8 silicon atoms. Exemplary linear volatile silicones include the Dow Corning DC 200 series with viscosities of 0.65 cst, 1.0 cst, and 2.0 cst. In certain embodiments, the linear volatile silicones generally have viscosities of less than or equal to about 4 centistokes at 25° C., and the cyclic materials generally have viscosities of less than about 6 centistokes at 25° C.

Also suitable volatile oils are volatile hydrocarbons. Examples of suitable volatile hydrocarbon oils include, but are not limited to, isododecane (e.g., Permethyl-99A which is available from Presperse Inc.), isodecane, and the C7-C8 through C12-C15 isoparaffins (e.g., Isopar Series available from Exxon Chemicals).

Thickening Agent

The composition of the present invention may include one or more thickening agents. The composition of the present invention may comprise from about 0.1% to about 5%, or, alternatively, from about 0.3% to about 3%, of a thickening agent when present. Suitable classes of thickening agents include but are not limited to carboxylic acid polymers, polyacrylamide polymers, sulfonated polymers, copolymers thereof, hydrophobically modified derivatives thereof, and mixtures thereof.

Suitable thickening agents include carboxylic acid polymers such as the carbomers (e.g., the CARBOPOL® 900 series such as CARBOPOL® 954), and Ultrez 10 and Ultrez 30. Other suitable carboxylic acid polymeric agents include copolymers of $C_{10-30}$ alkyl acrylates with one or more monomers of acrylic acid, methacrylic acid, or one of their short chain (i.e., $C_{1-4}$ alcohol) esters, wherein the crosslinking agent is an allyl ether of sucrose or pentaerytritol. These copolymers are known as acrylates/$C_{10-30}$ alkyl acrylate crosspolymers and are commercially available as CARBOPOL® 1342, CARBOPOL® 1382, Ultrez 20, Ultrez 21, PEMULEN TR-1, and PEMULEN TR-2, from Noveon, Inc.

Other suitable thickening agents include the polyacrylamide polymers and copolymers. An exemplary polyacrylamide polymer has the CTFA designation "polyacrylamide and isoparaffin and laureth-7" and is available under the trade name SEPIGEL 305 from Seppic Corporation (Fairfield, N.J.). Other polyacrylamide polymers useful herein include multi-block copolymers of acrylamides and substituted acrylamides with acrylic acids and substituted acrylic acids. Commercially available examples of these multi-block copolymers include HYPAN SR150H, SS500V, SS500 W, SSSA100H, from Lipo Chemicals, Inc., (Patterson, N.J.).

Other suitable thickening agents useful herein are sulfonated polymers such as the CTFA designated sodium polyacryloyldimethyl taurate available under the trade name Simulgel 800 from Seppic Corp. and Viscolam At 100 P available from Lamberti S.p.A. (Gallarate, Italy). Another commercially available material comprising a sulfonated polymer is Sepiplus 400 available from Seppic Corp.

Further, suitable thickeners may include superabsorbent polymers. These superabsorbent polymers may be chosen from: crosslinked sodium polyacrylates, such as, for example, those sold under the names Octacare X100, X110 and RM100 by Avecia, those sold under the names Flocare GB300 and Flosorb 500 by SNF, those sold under the names Luquasorb 1003, Luquasorb 1010, Luquasorb 1280 and Luquasorb 1100 by BASF, those sold under the names Water Lock G400 and G430 (INCI name: Acrylamide/Sodium Acrylate Copolymer) by Grain Processing, or Aqua Keep 10 SH NF, Aqua Keep 10 SH NFC, sodium acrylate crosspolymer-2, provided by Sumitomo Seika, starches grafted by an acrylic polymer (homopolymer or copolymer) and in particular by sodium polyacrylate, such as those sold under the names Sanfresh ST-100C, ST100MC and IM-300MC by Sanyo Chemical Industries (INCI name: Sodium Polyacrylate Starch), hydrolysed starches grafted by an acrylic polymer (homopolymer or copolymer), in particular the acryloacrylamide/sodium acrylate copolymer, such as those sold under the names Water Lock A-240, A-180, B-204, D-223, A-100, C-200 and D-223 by Grain Processing (INCI name: Starch/Acrylamide/Sodium Acrylate Copolymer). Preferred superabsorbent polymers include Makimousse 12 and Makimouse 25 supplied by Kobo Products Inc.

Suitable thickeners for use herein include gums. "Gum" is a broadly defined term in the art. Gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, derivatives thereof and mixtures thereof.

Natural gums are polysaccharides of natural origin, capable of causing a large viscosity increase in solution, even at small concentrations. They can be used as thickening agents, gelling agents, emulsifying agents, and stabilizers. Most often these gums are found in the woody elements of plants or in seed coatings. Natural gums can be classified according to their origin. They can also be classified as uncharged or ionic polymers (polyelectrolytes), examples of which include the following. Natural gums obtained from seaweeds, such as: agar; alginic acid; sodium alginate; and carrageenan. Natural gums obtained from non-marine botanical resources include: gum arabic, from the sap of *Acacia* trees; gum ghatti, from the sap of *Anogeissus* trees; gum tragacanth, from the sap of *Astragalus* shrubs; karaya gum, from the sap of *Sterculia* trees. Examples of uncharged gums include: guar gum, from guar beans, locust bean gum, from the seeds of the carob tree; beta-glucan, from oat or barley bran; chicle gum, an older base for chewing gum obtained from the chicle tree; dammar gum, from the sap of Dipterocarpaceae trees; glucomannan from the konjac plant; mastic gum, a chewing gum from ancient Greece obtained from the mastic tree; *psyllium* seed husks, from the *Plantago* plant; spruce gum, a chewing gum of American Indians obtained from spruce trees; tara gum, from the seeds of the tara tree. Natural gums produced by bacterial fermentation include gellan gum and xanthan gum.

Non-Spherical Silicone Elastomer

The compositions of the present invention may comprise a non-spherical silicone elastomer. Silicone elastomers are useful for reducing the tackiness of the composition and for providing a pleasant feel upon application. One non-limiting example of a suitable class of silicone elastomers is cross-linked organopolysiloxane (or siloxane) elastomers, which are generally described in U.S. patent application publication US2003/0049212A1.

The composition of the present invention may comprise from about 0.1% to about 5% or, alternatively, from about 0.5% to about 2% of one or more silicone elastomers. The indicated percentages are understood to refer to amount of dry elastomer, as opposed to the total amount of elastomer and solvent, used for example for storage and shipping.

Exemplary non-spherical crosslinked siloxane elastomers include the CTFA (Cosmetic, Toiletry, and Fragrance Association *International Cosmetic Ingredient Dictionary and Handbook*, 11$^{th}$ ed.) designated dimethicone/vinyl dimethicone crosspolymers supplied by a variety of suppliers including Dow Corning™, General Electric™, Shin Etsu™ (KSG 15 and 16), and Grant Industries. Other exemplary non-emulsifying crosslinked siloxane elastomer include the CTFA designated dimethicone crosspolymers including Dow Corning™; e.g. DC 9040 and DC 9045 which are supplied as a 12.5% elastomers in cyclodimeticone, and DC 9041 which is supplied as 16% elastomer in dimeticone).

Actives

The composition of the present invention may comprise at least one skin care active ("active"), useful for regulating and/or improving the condition of mammalian skin. The active may be soluble in oil or water, and may be present primarily in the oil phase and/or in the aqueous phase. Solubility in water and oil is within the knowledge of one of skill in the art, and can be determined using known methods of analysis. One of skill in the art further will understand that solubility may be affected by the type and concentration of other components in the composition, and other conditions such as pH, ionic strength, etc. Many skin care actives may provide more than one benefit, or operate via more than one mode of action; therefore, classifications herein are made for the sake of convenience and are not intended to limit the active to that particular application or applications listed. Suitable actives include, but are not limited to, vitamins, peptides, sugar amines, oil control agents, tanning actives, anti-acne actives, desquamation actives, anti-cellulite actives, chelating agents, skin lightening agents, flavonoids, protease inhibitors, non-vitamin antioxidants and radical scavengers, hair growth regulators, anti-wrinkle actives, anti-atrophy actives, minerals, phytosterols and/or plant hormones, tyrosinase inhibitors, anti-inflammatory agents, N-acyl amino acid compounds, antimicrobials, and antifungals.

The compositions of the present invention may comprise from about 0.001% to about 10%, alternatively from about 0.01% to about 5%, of at least one vitamin. Herein, "vitamins" means vitamins, pro-vitamins, and their salts, isomers and derivatives. Non-limiting examples of suitable vitamins include: vitamin B compounds (including B1 compounds, B2 compounds, B3 compounds such as niacinamide, niacinnicotinic acid, tocopheryl nicotinate, C1-C18 nicotinic acid esters, and nicotinyl alcohol; B5 compounds, such as panthenol or "pro-B5", pantothenic acid, pantothenyl; B6 compounds, such as pyroxidine, pyridoxal, pyridoxamine; carnitine, thiamine, riboflavin); vitamin A compounds, and all natural and/or synthetic analogs of Vitamin A, including retinoids, retinol, retinyl acetate, retinyl palmitate, retinoic acid, retinaldehyde, retinyl propionate, carotenoids (pro-vitamin A), and other compounds which possess the biological activity of Vitamin A; vitamin D compounds; vitamin K compounds; vitamin E compounds, or tocopherol, including tocopherol sorbate, tocopherol acetate, other esters of tocopherol and tocopheryl compounds; vitamin C compounds, including ascorbate, ascorbyl esters of fatty acids, and ascorbic acid derivatives, for example, ascorbyl phosphates such as magnesium ascorbyl phosphate and sodium ascorbyl phosphate, ascorbyl glucoside, and ascorbyl sorbate; and vitamin F compounds, such as saturated and/or unsaturated fatty acids. In one embodiment, the composition comprises a vitamin selected from the group consisting of vitamin B compounds, vitamin C compounds, vitamin E compounds and mixtures thereof. Alternatively, the vitamin is selected from the group consisting of niacinamide, tocopheryl nicotinate, pyroxidine, panthenol, vitamin E, vitamin E acetate, ascorbyl phosphates, ascorbyl glucoside, and mixtures thereof.

The compositions of the present invention may comprise one or more peptides. Herein, "peptide" refers to peptides containing ten or fewer amino acids, their derivatives, isomers, and complexes with other species such as metal ions (for example, copper, zinc, manganese, and magnesium). As used herein, peptide refers to both naturally occurring and synthesized peptides. In one embodiment, the peptides are di-, tri-, tetra-, penta-, and hexa-peptides, their salts, isomers, derivatives, and mixtures thereof. Examples of useful peptide derivatives include, but are not limited to, peptides derived from soy proteins, carnosine (beta-alanine-histidine), palmitoyl-lysine-threonine (pal-KT) and palmitoyl-lysine-threonine-threonine-lysine-serine (pal-KTTKS, available in a composition known as MATRIXYL®), palmitoyl-glycine-glutamine-proline-arginine (pal-GQPR, available in a composition known as RIGIN®), these three being available from Sederma, France, acetyl-glutamate-glutamate-methionine-glutamine-arginine-arginine (Ac-EE-MQRR; Argireline®), and Cu-histidine-glycine-glycine (Cu-HGG, also known as IAMIN®). The compositions may comprise from about $1\times10^{-7}$% to about 20%, alternatively from about $1\times10^{-6}$% to about 10%, and alternatively from about $1\times10^{-5}$% to about 5% of the peptide.

Test Methods

Chroma Method

Herein, "chroma," describes color and color intensity. For the purposes of the present invention, color is defined according to a value on the CIELAB color system, which is based on the XYZ color system, defined by the Commission Internationale de l'Eclairage (CIE system) to provide a manner of objectively representing perceived color and color differences. X, Y and Z can be expressed in a variety of manners, or "scales," one of which is the Hunter scale. The Hunter scale has three variables, L, a, and b, which correlate mathematically to X, Y and Z, and is described by Robertson, A. R. in "The CIE 1976 Color Difference Formulas," *Color Research Applications*, vol. 2, pp. 7-11 (1977).

To measure the color of the compositions of the present invention, a thick, uniform film of the composition is first created on a standard background. Specifically, product is applied onto a standard opacity chart (Form N2A, Leneta Company of Manwah, N.J. or the equivalent thereof, of which the top half is black and the bottom half is white) and then spread on the black area of the opacity chart into a film having a thickness of approximately 0.01 inches using a film applicator (e.g., as commercially available from BYK Gardner of Columbia, Md., or the equivalent thereof).

The color (L, a, and b values) of the product film is then measured using a spectrophotometer with settings selected to exclude specular reflection. The value for "a" correlates to a value along the red-green (horizontal) axis, and the value for "b" correlates to a value along the blue-yellow (vertical) axis. For example, a blue-colored sample will have a negative b-value, whereas a red-colored sample will have a positive a-value. A more positive or negative value represents a more intense color. The value for "L" is an indicator of lightness and/or darkness, and correlates to a value along the z-axis, which is perpendicular to both the horizontal and vertical axes.

"Chroma" is measured by a vector having its origin at the intersection of the red-green and blue-yellow axes and extending outward into the color space defined by the horizontal and vertical axes of the CIELAB color system. The length of the vector represents the chroma, and the direction of the vector represents the shade, or hue. The shorter the vector, the less colored is the composition, and the lower the chroma. The chroma for the individual layers of the present invention, that is the chroma value for the first layer or the powder layer is less than about 10, preferably less than about 6, and even more preferably less than about 3.

Contrast Ratio

Herein, "contrast ratio" refers to the opacity of the composition, or the ability of the composition to reduce or prevent light transmission, determined after the composition is drawn onto an opacity chart (Form N2A, Leneta Company of Manwah, N.J. or the equivalent thereof), and by using a spectrophotometer with settings selected to exclude specular reflection. The composition is applied to the top of the opacity chart and then is drawn into a film having a thickness of approximately 0.01 inches using a film applicator (e.g., as commercially available from BYK Gardner of Columbia, Md., or the equivalent thereof). The film is allowed to dry for 2 hours under conditions of 22° C.+/−1° C., 1 atm. Using a spectrophotometer, the Y tristimulus value (i.e., the XYZ color space of the film) of the product film is measured and recorded. The Y tristimulus value is measured in three different areas of the product film over the black section of the opacity chart, and also in three different areas of the product film over the white section of the opacity chart.

The contrast ratio for the individual layers of the present invention, that is the contrast ratio for the first layer or the powder layer is less than about 20, preferably less than about 10, and even more preferably less than about 6.

The contrast ratio is calculated as the mathematical average of the three Y tristimulus values over the black areas, divided by the mathematical average of the three Y tristimulus values over the white areas, times 100:

$$\text{Contrast Ratio} = \frac{\text{average }(Yblack)}{\text{average }(Ywhite)} \times 100$$

Visual Attribute Test (VAT)

The visible attribute test (VAT) is a technical panel used to quantify visible benefits of the compositions of the present invention when applied to facial skin. Fifteen to thirty female panelists who are pre-screened to have moderate or higher baseline levels of facial attributes such as fine lines, wrinkles, bumpy surface texture, and pores participate in each VAT study. Two trained expert graders then grade various attributes on each panelist's face both at baseline and 10 minutes after application of 0.45 grams of product to one side of the face. Reductions in facial attributes are then calculated as pre-treatment grade minus the post-treatment grade, and the significance of the differences are determined using ANOVA procedures (Tukey's LSD test).

A hypothetical data table representing typical VAT data calculations for bumpy surface texture is below. For fine lines, wrinkles, bumpy surface texture and/or pores, a difference of greater than approximately 0.4 provides consumer noticeable changes.

| Panelist Number | Pre-Treatment Grade | Post-Treatment Grade | Delta (Pre Minus Post) |
|---|---|---|---|
| 1 | 3.65 | 3.15 | 0.5 |
| 2 | 3.5 | 2.95 | 0.55 |
| 3 | 4.1 | 3.2 | 0.9 |
| 4 | 4.5 | 3.85 | 0.65 |
| 5 | 3.7 | 2.8 | 0.9 |

The facial attributes evaluated by the expert graders include the following:

Lines/Wrinkles—Severity of the skin on the cheek areas caused by fine lines and wrinkles. The cheek area includes that which is below the top of the cheek bone, excluding skin around the mouth. Features of this attribute include the number, length, depth, and percent coverage of the lines and wrinkles. Does NOT encompass pores directly, but does include lines which appear to be formed by interconnected pores. Each of the features of this attribute are equally weighted.

Bumpy Surface—Skin unevenness or roughness associated with a "pebbled" or an "orange peel" surface. Based on both the degree of roughness as defined as height and proximity and the percentage of the face covered by the surfaced appearance. Roughness and coverage are equally weighted in the final grade. Does NOT include obviously raised brown moles.

Pores—Coverage and intensity of the facial pores. Coverage is defined as the percentage of the entire cheek areas that possess visible pores (open holes). Intensity is defined as the quantity of pores and the average pore size where larger pores drive higher scores. Both elements of this attribute are equally weighted in the final grade.

Brightness—The brightening feature increases the lightness and luminescence of the face. It may be accompanied by a reduction in red and brown tones.

The expert graders rate each of the above attributes both pre- and post-treatment using the 5 point continuous line scale shown in the FIGURE.

EXAMPLES

Examples 1-10

The following examples of the first layer compositions according to the present invention are prepared by first combining the water phase ingredients and mixing until uniform, warming if necessary. Next, the thickeners are added and the composition is again mixed until uniform. Finally, the pH adjustor, if present, is added and composition is mixed until uniform.

| | Example 1 First Layer | Example 2 First Layer | Example 3 First Layer | Example 4 First Layer | Example 5 First Layer |
|---|---|---|---|---|---|
| Water Phase: | | | | | |
| Water | Qs | qs | qs | qs | Qs |
| Glycerin | 15.0 | 15.0 | 15.0 | 25.0 | 25.0 |
| Dipropylene Glycol | — | — | — | — | 5.0 |
| Butylene Glycol | — | — | 3.0 | — | — |
| Disodium EDTA | 0.05 | 0.05 | 0.05 | 0.05 | 0.05 |
| Symdiol 68[1] | 0.7 | 0.7 | 0.7 | 0.7 | 0.7 |
| Glycacil L[2] | 0.09 | 0.09 | 0.09 | 0.09 | 0.09 |
| Phenoxyethanol | — | — | — | 0.5 | — |
| Niacinamide | 5.0 | 5.0 | 2.0 | 3.5 | 1.0 |
| D-panthenol | 0.5 | 1.0 | 0.25 | 0.5 | — |
| Sepiwhite MSH[3] | 0.2 | 0.5 | — | — | — |
| Glyco-Repair[4] | 3.0 | — | 1.0 | — | 2.0 |
| Biomyox[5] | 2.0 | 0.5 | — | — | 1.0 |
| Palmitoyl-pentapeptide[6] | 0.01 | — | — | — | — |
| N-acetyl glucosamine | — | — | — | 2.0 | 0.5 |
| Inositol | 1.0 | 0.5 | — | — | — |
| Olivem 460[7] | — | — | 0.1 | — | — |
| Aloe Vera Gel | — | 0.2 | — | — | 0.5 |
| Green Tea Extract | 0.5 | — | — | 1.0 | — |
| pH Adjustor: | | | | | |
| Triethanolamine | 0.1 | 0.3 | — | — | 0.2 |
| Thickener: | | | | | |
| Sepigel 305[8] | 2.0 | — | — | — | — |
| Simulgel INS-100[9] | — | 2.5 | 1.5 | — | 1.0 |
| Makimousse-12[10] | — | — | — | 0.6 | — |
| Ultrez 10[11] | — | — | — | — | 0.2 |
| Total: | 100% | 100% | 100% | 100% | 100% |

[1]1,2-hexanediol and caprylyl glycol, from Symrise
[2]Iodopropynyl butylcarbamate, PEG-4 laurate, PEG-4 dilaurate, and polyethylene glycol, from Lonza
[3]Undecylenoyl phenylalanine, from Seppic
[4]Water and hydrolyzed ceratonia siliqua seed extract, from Silab
[5]Water and nasturtrium officinale extract, from Silab
[6]Palmitoyl-lysine-threonine-threonine-lysine-serine available from Sederma (France)
[7]Sodium PEG-7 olive oil carboxylate, from B&T S.r.l.
[8]Polyacrylamide, C13-14 isoparaffin, and laureth-7, from Seppic
[9]Sodium acrylate/sodium acryloyldimethyl taurate copolymer, isohexadecane, and polysorbate 60, from Seppic
[10]Sodium polyacrylate starch, from Kobo Products Inc.
[11]Carbomer, from Lubrizol

|  | Example 6 First Layer | Example 7 First Layer | Example 8 First Layer | Example 9 First Layer | Example 10 First Layer |
| --- | --- | --- | --- | --- | --- |
| Water Phase: | | | | | |
| Water | Qs | qs | qs | qs | Qs |
| Glycerin | 15.0 | 15.0 | 10.0 | 10.0 | 10.0 |
| Propylene Glycol | 3.0 | 5.0 | — | 5.0 | 5.0 |
| Dipropylene Glycol | 3.0 | — | 10.0 | 5.0 | 2.0 |
| Butylene Glycol | 3.0 | — | — | 5.0 | — |
| Disodium EDTA | 0.05 | 0.05 | 0.05 | 0.05 | 0.05 |
| Methylparaben | 0.1 | — | — | — | — |
| Symdiol 68[1] | — | 0.7 | 0.7 | 0.7 | — |
| Sodium Benzoate | 0.1 | — | — | — | — |
| Glycacil L[2] | — | 0.09 | 0.09 | 0.09 | — |
| Phenoxyethanol | 0.5 | 0.1 | — | — | — |
| Glydant Plus Liquid[3] | — | — | — | — | 0.3 |
| Niacinamide | 3.0 | 2.0 | — | — | — |
| D-panthenol | 0.7 | 0.3 | 0.5 | — | — |
| Glyco-Repair[4] | — | — | — | — | 1.0 |
| Biomyox[5] | — | 1.5 | — | — | — |
| Palmitoyl-pentapeptide[6] | 0.03 | — | — | — | 0.01 |
| N-acetyl glucosamine | — | — | 1.0 | — | — |
| Aloe Vera Gel | — | — | — | — | 0.1 |
| Green Tea Extract | — | 0.5 | — | — | 0.1 |
| pH Adjustor: | | | | | |
| Triethanolamine | — | 0.3 | — | — | — |
| Aminomethyl propanol | — | — | — | 0.1 | 0.1 |
| Thickener: | | | | | |
| Simulgel INS-100[7] | 2.5 | — | — | 0.5 | — |
| Makimousse-7[8] | — | — | — | — | 0.6 |
| Makimousse-12[9] | — | — | 0.4 | 0.3 | — |
| Ultrez 10[10] | — | — | — | 0.1 | — |
| Ultrez 21[11] | — | 0.3 | — | — | — |
| Xanthan gum | — | — | 0.1 | — | — |
| Total: | 100% | 100% | 100% | 100% | 100% |

[1] 1,2-hexanediol and caprylyl glycol, from Symrise
[2] Iodopropynyl butylcarbamate, PEG-4 laurate, PEG-4 dilaurate, and polyethylene glycol, from Lonza
[3] DMDM Hydantoin, Butane-1,3-diol, iodopropynyl butylcarbamate, water, from Lonza
[4] Water and hydrolyzed ceratonia siliqua seed extract, from Silab
[5] Water and nasturtrium officinale extract, from Silab
[6] Palmitoyl-lysine-threonine-threonine-lysine-serine available from Sederma (France)
[7] Sodium acrylate/sodium acryloyldimethyl taurate copolymer, isohexadecane, and polysorbate 60, from Seppic
[8] Sodium polyacrylate starch, from Kobo Products Inc.
[9] Sodium polyacrylate starch, from Kobo Products Inc.
[10] Carbomer, from Lubrizol
[11] Acrylates C10-/30 alkyl acrylate crosspolymer, from Lubrizol Examples 11-25

The following examples of the powder layer compositions according to the present invention are prepared by first combining the water phase ingredients in a container and mixing until uniform. The thickener is added and the water phase is mixed until uniform, and then the pH adjuster, if present, is added and the water phase is again mixed until uniform. The oil phase ingredients are combined in a separate container and mixed until uniform. The powders are next added to the oil phase and the combination is mixed until uniform. Finally, the oil/powder phase is added to the water phase and the resulting emulsion is subjected to high shear mixing (e.g., Flacktek Speedmixer, or rotor-stator mill).

|  | Example 11 Powder Layer | Example 12 Powder Layer | Example 13 Powder Layer | Example 14 Powder Layer | Example 15 Powder Layer |
| --- | --- | --- | --- | --- | --- |
| Water Phase: | | | | | |
| Water | Qs | qs | Qs | qs | Qs |
| Disodium EDTA | 0.05 | 0.05 | 0.05 | 0.05 | 0.05 |
| Methylparaben | — | — | — | 0.1 | — |
| Symdiol 68[1] | 0.7 | 0.7 | 0.7 | — | — |
| Glycacil L[2] | 0.09 | 0.09 | 0.09 | 0.09 | — |
| Phenoxyethanol | — | — | 0.2 | 0.5 | — |
| Glydant Plus Liquid[3] | — | — | — | — | 0.3 |
| pH Adjustor: | | | | | |
| Triethanolamine | — | — | — | 0.2 | — |
| Thickener: | | | | | |
| Sepigel 305[4] | — | — | 0.5 | 1.0 | — |
| Simulgel INS-100[5] | 2.0 | 1.5 | 1.0 | — | — |
| Makimousse-12[6] | — | — | — | — | 0.4 |
| Ultrez 10[7] | — | — | — | 0.1 | — |
| Ultrez 21[8] | — | — | — | 0.1 | — |
| Xanthan gum | — | — | — | — | 0.1 |
| Oil Phase: | | | | | |
| Cyclomethicone D5 | 6.0 | 12.0 | — | 5.0 | 10.0 |
| Dimethicone 2 cst | — | — | 5.0 | — | — |
| Dimethicone 20 cst | — | — | 3.0 | — | — |
| Dimethicone 50 cst | 10.0 | 10.0 | — | 12.0 | 8.0 |
| Dimethicone 350 cst | — | — | 3.0 | — | — |
| DE-23[9] | — | — | 3.0 | — | — |
| DC 5562[10] | — | — | — | — | 2.0 |
| DC1503[11] | — | — | — | — | 2.0 |
| DC9045[12] | 11.0 | — | 4.0 | — | — |
| Laureth-4 | 0.3 | 0.3 | 0.3 | 0.3 | 0.3 |
| Particles: | | | | | |
| Dry Flo TS[13] | 20.0 | 25.0 | 15.0 | — | 10.0 |
| Tapioca Pure[14] | — | — | — | 20.0 | 5.0 |
| Dry Flo Pure[15] | — | — | — | — | 5.0 |
| Total: | 100% | 100% | 100% | 100% | 100% |

[1] 1,2-hexanediol and caprylyl glycol, from Symrise
[2] Iodopropynyl butylcarbamate, PEG-4 laurate, PEG-4 dilaurate, and polyethylene glycol, from Lonza
[3] DMDM Hydantoin, Butane-1,3-diol, iodopropynyl butylcarbamate, water, from Lonza
[4] Polyacrylamide, C13-14 isoparaffin, and laureth-7, from Seppic
[5] Sodium acrylate/sodium acryloyldimethyl taurate copolymer, isohexadecane, and polysorbate 60, from Seppic
[6] Sodium polyacrylate starch, from Kobo Products Inc.
[7] Carbomer, from Lubrizol
[8] Acrylates C10-/30 alkyl acrylate crosspolymer, from Lubrizol
[9] Polydiethylsiloxane, from Gelest
[10] Bis-hydroxyethoxypropyl dimethicone, from Dow Corning
[11] Dimethicone and dimethiconol, from Dow Corning
[12] Cyclopentasiloxane and dimethicone crosspolymer, from Dow Corning
[13] Tapioca and polymethylsilsesquioxane, from Akzo Nobel
[14] Tapioca powder, from Akzo Nobel
[15] Aluminum starch octenyl succinate, from Akzo Nobel

|  | Example 16 Powder Layer | Example 17 Powder Layer | Example 18 Powder Layer | Example 19 Powder Layer | Example 20 Powder Layer |
| --- | --- | --- | --- | --- | --- |
| Water Phase: | | | | | |
| Water | Qs | qs | qs | qs | qs |
| Disodium EDTA | 0.05 | 0.05 | 0.05 | 0.05 | 0.05 |
| Methylparaben | — | — | — | 0.1 | — |
| Symdiol 68[1] | 0.7 | 0.7 | 0.7 | — | — |
| Glycacil L[2] | 0.09 | 0.09 | 0.09 | 0.09 | — |
| Phenoxyethanol | — | — | 0.2 | 0.5 | — |
| Glydant Plus Liquid[3] | — | — | — | — | 0.3 |

-continued

|  | Example 16 Powder Layer | Example 17 Powder Layer | Example 18 Powder Layer | Example 19 Powder Layer | Example 20 Powder Layer |
|---|---|---|---|---|---|
| pH Adjustor: | | | | | |
| Triethanolamine | — | — | — | 0.2 | — |
| Thickener: | | | | | |
| Sepigel 305[4] | — | — | 0.5 | 1.0 | — |
| Simulgel INS-100[5] | 2.0 | 1.5 | 1.0 | — | — |
| Makimousse-12[6] | — | — | — | — | 0.4 |
| Ultrez 10[7] | — | — | — | 0.1 | — |
| Ultrez 21[8] | — | — | — | 0.1 | — |
| Xanthan gum | — | — | — | — | 0.1 |
| Oil Phase: | | | | | |
| Cyclomethicone D5 | 11.0 | 16.0 | — | 15.0 | 14.0 |
| Dimethicone 2 cst | — | — | 12.0 | — | — |
| Dimethicone 20 cst | — | — | 3.0 | — | — |
| Dimethicone 50 cst | 11.0 | 10.0 | — | 10.0 | 8.0 |
| Dimethicone 350 cst | — | — | 3.0 | — | — |
| DE-23[9] | — | — | 3.0 | — | — |
| DC 5562[10] | — | — | — | — | 2.0 |
| DC1503[11] | — | — | — | — | 2.0 |
| DC9045[12] | 4.0 | — | — | — | — |
| Laureth-4 | 0.3 | 0.3 | 0.3 | 0.3 | 0.3 |
| Particles: | | | | | |
| Dry Flo TS[13] | 15.0 | 10.0 | 6.0 | — | — |
| Tapioca Pure[14] | — | — | — | 10.0 | — |
| Dry Flo Pure[15] | — | — | — | — | 5.0 |
| KSP 100[16] | — | 10.0 | — | — | 10.0 |
| KSP 101[17] | 5.0 | — | — | — | — |
| KSP 102[18] | — | — | 3.0 | — | — |
| KSP 103[19] | — | — | — | 10.0 | — |
| KSP 105[20] | — | — | 3.0 | — | 5.0 |
| DC9506[21] | — | — | 6.0 | — | — |
| Total: | 100% | 100% | 100% | 100% | 100% |

[1] 1,2-hexanediol and caprylyl glycol, from Symrise
[2] Iodopropynyl butylcarbamate, PEG-4 laurate, PEG-4 dilaurate, and polyethylene glycol, from Lonza
[3] DMDM Hydantoin, Butane-1,3-diol, iodopropynyl butylcarbamate, water, from Lonza
[4] Polyacrylamide, C13-14 isoparaffin, and laureth-7, from Seppic
[5] Sodium acrylate/sodium acryloyldimethyl taurate copolymer, isohexadecane, and polysorbate 60, from Seppic
[6] Sodium polyacrylate starch, from Kobo Products Inc.
[7] Carbomer, from Lubrizol
[8] Acrylates C10-/30 alkyl acrylate crosspolymer, from Lubrizol
[9] Polydiethylsiloxane, from Gelest
[10] Bis-hydroxyethoxylpropyl dimethicone, from Dow Corning
[11] Dimethicone and dimethiconol, from Dow Corning
[12] Cyclopentasiloxane and dimethicone crosspolymer, from Dow Corning
[13] Tapioca and polymethylsilsesquioxane, from Akzo Nobel
[14] Tapioca powder, from Akzo Nobel
[15] Aluminum starch octenyl succinate, from Akzo Nobel
[16] Vinyl dimethicone/methicone silsesquioxane crosspolymer, from Shin Etsu
[17] Vinyl dimethicone/methicone silsesquioxane crosspolymer, from Shin Etsu
[18] Vinyl dimethicone/methicone silsesquioxane crosspolymer, from Shin Etsu
[19] Vinyl dimethicone/methicone silsesquioxane crosspolymer, from Shin Etsu
[20] Vinyl dimethicone/methicone silsesquioxane crosspolymer, from Shin Etsu
[21] Dimethicone/Vinyl dimethicone crosspolymer, from Dow Corning

|  | Example 21 Powder Layer | Example 22 Powder Layer | Example 23 Powder Layer | Example 24 Powder Layer | Example 25 Powder Layer |
|---|---|---|---|---|---|
| Water Phase: | | | | | |
| Water | Qs | qs | qs | qs | Qs |
| Disodium EDTA | 0.05 | 0.05 | 0.05 | 0.05 | 0.05 |
| Methylparaben | — | — | — | 0.1 | — |
| Symdiol 68[1] | 0.7 | 0.7 | 0.7 | — | — |
| Glycacil L[2] | 0.09 | 0.09 | 0.09 | 0.09 | — |
| Phenoxyethanol | — | — | 0.2 | 0.5 | — |
| Glydant Plus Liquid[3] | — | — | — | — | 0.3 |
| pH Adjustor: | | | | | |
| Triethanolamine | — | — | — | 0.2 | — |
| Thickener: | | | | | |
| Sepigel 305[4] | — | — | 0.6 | 1.0 | — |
| Simulgel INS-100[5] | 2.0 | 1.5 | 1.0 | — | 0.7 |
| Makimousse-12[6] | — | — | — | — | 0.3 |
| Ultrez 10[7] | — | — | — | 0.1 | — |
| Ultrez 21[8] | — | — | — | 0.1 | — |
| Xanthan gum | — | — | — | — | 0.1 |
| Oil Phase: | | | | | |
| Cyclomethicone D5 | 18.0 | 16.0 | — | 16.0 | 18.0 |
| Dimethicone 2 cst | — | — | 12.0 | — | — |
| Dimethicone 20 cst | — | — | 3.0 | — | — |
| Dimethicone 50 cst | 8.0 | 10.0 | — | 6.0 | 6.0 |
| Dimethicone 350 cst | — | — | 3.0 | 2.0 | — |
| DE-23[9] | — | — | 3.0 | — | — |
| DC 5562[10] | — | — | — | — | 2.0 |
| DC1503[11] | — | — | — | — | 2.0 |
| DC9045[12] | — | 4.0 | — | — | — |
| Laureth-4 | 0.3 | 0.3 | 0.3 | 0.3 | 0.3 |
| Particles: | | | | | |
| KSP 100[13] | 15.0 | — | 10 | 5.0 | — |
| KSP 101[14] | — | — | — | 5.0 | — |
| KSP 102[15] | — | 10.0 | — | — | — |
| KSP 103[16] | — | — | — | 5.0 | — |
| KSP 105[17] | — | 10.0 | 10 | — | 6.0 |
| DC9506[18] | — | — | — | — | 10.0 |
| Total: | 100% | 100% | 100% | 100% | 100% |

[1] 1,2-hexanediol and caprylyl glycol, from Symrise
[2] Iodopropynyl butylcarbamate, PEG-4 laurate, PEG-4 dilaurate, and polyethylene glycol, from Lonza
[3] DMDM Hydantoin, Butane-1,3-diol, iodopropynyl butylcarbamate, water, from Lonza
[4] Polyacrylamide, C13-14 isoparaffin, and laureth-7, from Seppic
[5] Sodium acrylate/sodium acryloyldimethyl taurate copolymer, isohexadecane, and polysorbate 80, from Seppic
[6] Sodium polyacrylate starch, from Kobo Products Inc.
[7] Carbomer, from Lubrizol
[8] Acrylates C10-/30 alkyl acrylate crosspolymer, from Lubrizol
[9] Polydiethylsiloxane, from Gelest
[10] Bis-hydroxyethoxylpropyl dimethicone, from Dow Corning
[11] Dimethicone and dimethiconol, from Dow Corning
[12] Cyclopentasiloxane and dimethicone crosspolymer, from Dow Corning
[13] Vinyl dimethicone/methicone silsesquioxane crosspolymer, from Shin Etsu
[14] Vinyl dimethicone/methicone silsesquioxane crosspolymer, from Shin Etsu
[15] Vinyl dimethicone/methicone silsesquioxane crosspolymer, from Shin Etsu
[16] Vinyl dimethicone/methicone silsesquioxane crosspolymer, from Shin Etsu
[17] Vinyl dimethicone/methicone silsesquioxane crosspolymer, from Shin Etsu
[18] Dimethicone/Vinyl dimethicone crosspolymer, from Dow Corning Example numbers 26-29 are intentionally left blank.

Comparative Examples

All data provided below is measured according to the VAT test described above and is statistically significant to an 80% confidence level (at alpha=0.20, Tukey tests). The number of participants graded according to the VAT method, in each Comparative Example, is given in table below.

| Comparative Example | Base Size (number of participants) |
|---|---|
| Examples 30-31 | 30 |
| Examples 32-36 | 17 |
| Examples 37-38 | 17 |
| Example 39 | 17 |
| Examples 40-41 | 10 |

Comparative Examples 30 and 31—Impact of Glycerin

The following two examples demonstrate the negative effects of combining a high moisturizing composition with a high particulate composition in an "all-in-one" composition. Accordingly, this comparison demonstrates the negative effect of high levels of humectant on the optical benefit of spherical powders when combined in a single ("all-in-one") composition. Both compositions 30 and 31 contain the same high level of silicone elastomer particles and non-volatile silicone oil, and are otherwise identical except that example 30 contains 5% glycerin while example 31 contains 25% glycerin.

Compositions 30 and 31 are prepared by first combining the water phase ingredients and thickener in a container and mixing until uniform. The oil phase ingredients are combined in a separate container and mixed until uniform. The particulates are next added to the oil phase and the combination is mixed until uniform. Finally, the oil/particulate phase is added to the water phase and the resulting emulsion is subjected to high shear mixing (e.g., Flacktek Speedmixer, or rotor-stator mill).

| | Example 30 | Example 31 |
|---|---|---|
| Water Phase: | | |
| Water | 20.84 | 0.84 |
| Glycerin | 5.0 | 25.0 |
| Disodium EDTA | 0.05 | 0.05 |
| Glydant Plus Liquid[1] | 0.3 | 0.3 |
| Niacinamide | 2.0 | 2.0 |
| D-panthenol | 0.5 | 0.5 |
| Laureth-4 | 0.2 | 0.2 |
| Thickener: | | |
| Simulgel INS-100[2] | 2.0 | 2.0 |
| Oil Phase: | | |
| Cyclomethicone D5 | 24.2 | 22.42 |
| Dimethicone 50 cst | 4.39 | 4.39 |
| DC9045[3] | 11.0 | 11.0 |
| Isopropyl lauroyl sarcosinate | 7.32 | 7.32 |
| Polysorbate 60 | 0.2 | 0.2 |
| Particles: | | |
| KSP 102[4] | 11.0 | 11.0 |
| KSP 105[5] | 11.0 | 11.0 |
| Total: | 100% | 100% |

[1]DMDM Hydantoin, Butane-1,3-diol, iodopropynyl butylcarbamate, water, from Lonza
[2]Sodium acrylate/sodium acryloyldimethyl taurate copolymer, isohexadecane, and polysorbate 60, from Seppic
[3]Cyclopentasiloxane and dimethicone crosspolymer, from Dow Corning
[4]Vinyl dimethicone/methicone silsesquioxane crosspolymer, from Shin Etsu
[5]Vinyl dimethicone/methicone silsesquioxane crosspolymer, from Shin Etsu Compositions 30 and 31 are then placed in a Visual Attribute Test (VAT) to compare their effectiveness at reducing the appearance of various facial attributes. As can be seen from the results of this testing, summarized in the table below, increasing the level of glycerin from 5% to 25% significantly reduced the optical benefit provided by the elastomer particles and non-volatile silicone oil combination in these products.

Larger VAT scores for cheek fine lines, bumpy surface, and pores correspond to bigger visible reductions in the appearance of these attributes. Thus, this data clearly demonstrates the negative impact that high levels of glycerin has on the optical benefits when combined with the particle and non-volatile oil systems in an "all-in-one" composition.

| | Example 30 5% Glycerin All-In-One | Example 31 25% Glycerin All-In-One |
|---|---|---|
| Cheek Fine Lines | 0.40 | 0.18 |
| Bumpy Surface | 0.29 | 0.09 |
| Pores | 0.27 | 0.09 |

Comparative Examples 32-36—Impact of Layers

Examples 32, 33, and 36 are prepared using the same process used for examples 30 and 31 above. Examples 34 and 35 are prepared by combining all of the water phase ingredients and pH adjuster and mixing until uniform, warming if necessary. Next, the thickeners are added and the composition is again mixed until uniform.

| | Example 32 Comparative All-in-One | Example 33 Comparative All-in-One W/Actives | Example 34 Inventive First Layer | Example 35 Inventive First Layer W/Actives | Example 36 Inventive Powder Layer |
|---|---|---|---|---|---|
| Water Phase: | | | | | |
| Water | 38.36 | 28.78 | 76.685 | 68.88 | 49.36 |
| Glycerin | 15.0 | 15.0 | 15.0 | 15.0 | — |
| Disodium EDTA | 0.05 | 0.05 | 0.025 | 0.05 | 0.05 |
| Symdiol 68[1] | 0.7 | 1.0 | 0.7 | 1.0 | 0.7 |
| Glycacil L[2] | 0.09 | 0.09 | 0.09 | 0.09 | 0.09 |
| Niacinamide | 5.0 | 5.0 | 5.0 | 5.0 | — |
| D-panthenol | 0.5 | 1.0 | 0.5 | 1.0 | — |
| Sepiwhite MSH[3] | — | 0.2 | — | 0.2 | — |
| Glyco-Repair[4] | — | 3.0 | — | 3.0 | — |
| Biomyox[5] | — | 2.0 | — | 2.0 | — |
| Palestrina[6] | — | 1.15 | — | 1.15 | — |
| Inositol | — | 1.5 | — | 1.5 | — |
| pH Adjuster: | | | | | |
| Triethanolamine | — | 0.13 | — | 0.13 | — |
| Thickener: | | | | | |
| Simulgel INS-100[7] | 1.6 | 2.4 | 2.0 | — | 1.5 |
| Maki-mousse-12[8] | — | — | — | 1.0 | — |
| Oil Phase: | | | | | |
| Cyclomethicone D5 | 8.0 | 8.0 | — | — | 12.0 |
| Dimethicone 50 cst | 5.0 | 5.0 | — | — | 5.0 |

-continued

|  | Example 32 Comparative All-in-One | Example 33 Comparative All-in-One W/Actives | Example 34 Inventive First Layer | Example 35 Inventive First Layer W/Actives | Example 36 Inventive Powder Layer |
|---|---|---|---|---|---|
| DC1503[9] | — | — | — | — | — |
| DC9045[10] | 5.5 | 5.5 | — | — | 11.0 |
| Laureth-4 | 0.2 | 0.2 | — | — | 0.3 |
| Particles: |  |  |  |  |  |
| Dry Flo TS[11] | 20.0 | 20.0 | — | — | 20.0 |
| Total: | 100% | 100% | 100% | 100% | 100% |

[1]1,2-hexanediol and caprylyl glycol, from Symrise
[2]Iodopropynyl butylcarbamate, PEG-4 laurate, PEG-4 dilaurate, and polyethylene glycol, from Lonza
[3]Undecylenoyl phenylalanine, from Seppic
[4]Water and hydrolyzed ceratonia siliqua seed extract, from Silab
[5]Water and nasturtrium officinale extract, from Silab
[6]Water, glycerin, decyl glucoside, lactic acid, benzyl alcohol, and palmitoyl dipeptide-7, from Sederma (France)
[7]Sodium acrylate/sodium acryloyldimethyl taurate copolymer, isohexadecane, and polysorbate 60, from Seppic
[8]Sodium polyacrylate starch, from Kobo Products Inc.
[9]Dimethicone and dimethiconol, from Dow Corning
[10]Cyclopentasiloxane and dimethicone crosspolymer, from Dow Corning
[11]Tapioca and polymethylsilsesquioxane, from Akzo Nobel Composition 32 is an all-in-one, or single step formulation that contains the same glycerin and skin active levels, as well as the same starch powder and non-volatile silicone oil as the two layer system consisting of composition 34, the first layer, followed by composition 36, the powder layer. Similarly, the all-in-one, or single step composition 34 is similar to the two layer system consisting of composition 35, the first layer, followed by composition 36, the powder layer. Note that the difference between compositions 32 and 34 compared to compositions 33 and 35 is that the latter compositions contain additional skin active ingredients (Sepiwhite MSH, Glyco-Repair, Biomyox, Palestrina, and Inositol). These relationships between compositions 32 through 36 are summarized in the table below. Note also that for the all-in-one versus two step composition comparisons, few very minor formula adjustments were made to ensure adequate stability and physical properties. However, these minor formula adjustments are not expected to significantly impact the optical benefit of these formulations.

|  | All-in-One Composition | Two Step Composition |
|---|---|---|
| Low Skin Actives | Example 32 | Step 1: Example 34 |
|  |  | Step 2: Example 36 |
| High Skin Actives | Example 33 | Step 1: Example 35 |
|  |  | Step 2: Example 36 |

The all-in-one compositions above (examples 32, 33) and their corresponding two step compositions (examples 34/36, 35/36) were then placed in a Visual Attribute Test (VAT) to compare their effectiveness at reducing the appearance of various facial attributes. For simplicity and to increase statistical power, the results of both of these all-in-one to two step comparisons have been combined in the table below. As can be seen from the results of this testing, the two step systems created according to the present invention provide significantly greater visible benefits than their corresponding all-in-one systems, despite both all-in-one and two step systems containing the same starch powder and non-volatile silicones (note that negative values for brightness correspond to an increase in brightness of the facial skin). Thus, these results demonstrate the benefits of the two step approach of the present invention.

|  | All-in-One Compositions Examples 32 and 33 | Two Layer Systems Examples 34 and 36 Examples 35 and 36 |
|---|---|---|
| Bumpy Surface | 0.43 | 0.61 |
| Pores | 0.55 | 0.68 |
| Brightness | −0.34 | −0.62 |

Comparative Examples 37-38—Impact of Non-Volatile Oil to Powder Ratio

The following are examples of the powder layer compositions according to the present invention, both of which contain 20% starch particles, similar to example 36 above. The key difference between example 36 above and examples 37 and 38 below, is the non-volatile oil (50 cst dimethicone) to powder ratio. Please note that a few very minor adjustments were made to these formulations to ensure that they had similar physical properties and stability, but these adjustments are not expected to impact product performance. Examples 37 and 38 are prepared in the same manner as examples 30 and 31.

|  | Example 37 | Example 38 |
|---|---|---|
| Water Phase: |  |  |
| Water | 44.36 | 40.56 |
| Disodium EDTA | 0.05 | 0.05 |
| Symdiol 68[1] | 0.7 | 0.7 |
| Glycacil L[2] | 0.09 | 0.09 |
| Thickener: |  |  |
| Simulgel INS-100[3] | 1.5 | 1.3 |
| Oil Phase: |  |  |
| Cyclomethicone D5 | 12.0 | 6.0 |
| Dimethicone 50 cst | 10.0 | 20.0 |
| DC9045[4] | 11.0 | 11.0 |
| Laureth-4 | 0.3 | 0.3 |
| Particles: |  |  |
| Dry Flo TS[5] | 20.0 | 20.0 |
| Total: | 100% | 100% |

[1]1,2-hexanediol and caprylyl glycol, from Symrise
[2]Iodopropynyl butylcarbamate, PEG-4 laurate, PEG-4 dilaurate, and polyethylene glycol, from Lonza
[3]Sodium acrylate/sodium acryloyldimethyl taurate copolymer, isohexadecane, and polysorbate 60, from Seppic
[4]Cyclopentasiloxane and dimethicone crosspolymer, from Dow Corning
[5]Tapioca and polymethylsilsesquioxane, from Akzo Nobel The example 36, 37, and 38 compositions were then placed into a VAT study as part of a two step regimen, using the composition in example 34 as the first step for each test. As can be seen from the results of this testing, summarized in the table below, as the non-volatile oil-to-powder ratio increased, the optical benefit provided by these compositions significantly decreased. Thus, this data clearly shows the benefit of the preferred oil to powder ratio in the compositions of this invention.

|  | Example 34 and Example 36 | Example 34 and Example 37 | Example 34 and Example 38 |
|---|---|---|---|
| Non-Volatile Oil to Powder Ratio | 1:4 | 1:2 | 1:1 |
| Cheek Fine Lines | 0.67 | 0.54 | 0.36 |
| Bumpy Surface | 0.67 | 0.58 | 0.33 |
| Brightness | −0.70 | −0.50 | −0.27 |

Comparative Example 39—Impact of Order of Layers

The following composition, example 39, is made by first combining the water phase ingredients and mixing until uniform. Next, the thickener is added and the composition is again mixed until uniform.

|  | Example 39 |
|---|---|
| Water Phase: | |
| Water | 78.16 |
| Glycerin | 15.0 |
| Disodium EDTA | 0.05 |
| Symdiol 68[1] | 0.7 |
| Glycacil L[2] | 0.09 |
| Niacinamide | 5.0 |
| D-panthenol | 0.5 |
| Thickener: | |
| Makimousse-12[3] | 0.5 |
| Total: | 100% |

[1]1,2-hexanediol and caprylyl glycol, from Symrise
[2]Iodopropynyl butylcarbamate, PEG-4 laurate, PEG-4 dilaurate, and polyethylene glycol, from Lonza
[3]Sodium polyacrylate starch, from Kobo Products Inc.

Using the composition in example 39, along with the compositions in the previous examples 34 and 36, a VAT study was conducted to understand the impact of the order in which the layers of the two step systems of this invention are applied to skin. Specifically, the following two step systems were placed in the VAT study:

|  | Step 1 Composition | Step 2 Composition |
|---|---|---|
| According to the invention | 34 | 36 |
| Reversed order | 36 | 39 |

Note that example 34 and example 39 differ only in the thickener used, and this difference is not expected to have a significant impact on the optical benefit of these two step systems. As can be seen from the VAT results below, while the two step system used according to the present invention delivered large benefits for the various visible attributes, the two step composition in which the order of the steps was reversed provided significantly less visible benefit. Thus, these results confirm the importance of the order of application steps of the current invention.

|  | Reversed Application Step 1: Powder layer Step 2: First layer | Present Invention Step 1: First layer Step 2: Powder layer |
|---|---|---|
| Cheek Fine Lines | 0.35 | 0.67 |
| Bumpy Surface | 0.28 | 0.67 |
| Brightness | −0.23 | −0.70 |

Comparative Examples 40-41—Impact of Increased Opacity

The following two examples both contain the same high level of silicone elastomer spherical particles and non-volatile silicone oil, and are identical except that example 41 contains 3.43% pigments while example 40 does not contain pigments. The pigments used in example 41 resulted in increased opacity compared to example 40. Opacity is assessed by measuring contrast ratio (the higher the contrast ratio, the higher the level of opacity). Example 41 has a contrast ratio of 34, while example 40 has a contrast ratio of 4.3. Examples 40 and 41 are prepared using the same process used for examples 30 and 31 above.

|  | Example 40 | Example 41 |
|---|---|---|
| Water Phase: | | |
| Water | 21.04 | 21.04 |
| Glycerin | 5.0 | 5.0 |
| Disodium EDTA | 0.05 | 0.05 |
| Glydant Plus Liquid[1] | 0.3 | 0.3 |
| Niacinamide | 2.0 | 2.0 |
| D-panthenol | 0.5 | 0.5 |
| Thickener: | | |
| Simulgel INS-100[2] | 2.0 | 2.0 |
| Oil Phase: | | |
| Cyclomethicone D5 | 24.2 | 20.77 |
| Dimethicone 50 cst | 4.39 | 4.39 |
| DC9045[3] | 11.0 | 11.0 |
| Isononyl Isononanoate | 7.32 | 7.32 |
| Laureth-4 | 0.2 | 0.2 |
| Powders: | | |
| KSP 102[4] | 11.0 | 11.0 |
| KSP 105[5] | 11.0 | 11.0 |
| Pigments: | | |
| Titanium Dioxide[6] | — | 3.0 |
| Iron Oxides CI 77491[7] | — | 0.1 |
| Iron Oxides CI 77492[8] | — | 0.33 |
| Total: | 100% | 100% |

[1]DMDM Hydantoin, Butane-1,3-diol, iodopropynyl butylcarbamate, water, from Lonza
[2]Sodium acrylate/sodium acryloyldimethyl taurate copolymer, isohexadecane, and polysorbate 60, from Seppic
[3]Cyclopentasiloxane and dimethicone crosspolymer, from Dow Corning
[4]Vinyl dimethicone/methicone silsesquioxane crosspolymer, from Shin Etsu
[5]Vinyl dimethicone/methicone silsesquioxane crosspolymer, from Shin Etsu
[6]Titanium Dioxide, Isohexadecane, Polyhydroxystearic Acid, Triethoxycaprylylsilane
[7]Iron Oxides CI 77491, Cyclopentasiloxane, Methicone, PEG/PGG-18/18 Dimethicone
[8]Iron Oxides CI 77492, Cyclopentasiloxane, Methicone, PEG/PPG-18/18 Dimethicone The example 40 and 41 compositions were then placed in a Visual Attribute Test (VAT) to compare their effectiveness at reducing the appearance of various facial attributes. As can be seen from the results of this testing, summarized in the table below, increasing opacity (higher contrast ratio) by using high refractive index pigments significantly reduced the optical benefit provided by the elastomer powder and silicone oil combination in these products. Thus, this data clearly demonstrates the negative impact that increased opacity has on the optical benefits of the powder and oil systems of the present invention.

|  | Example 40<br>0% Pigment<br>Contrast Ratio = 4.3 | Example 41<br>3.43% Pigment<br>Contrast Ratio = 34 |
| --- | --- | --- |
| Cheek Fine Lines | 0.64 | 0.03 |
| Bumpy Surface | 0.65 | −0.03 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of using a multi-layer product comprising the steps of;
    a. applying to human skin a first layer comprising from about 8% to about 30%, by weight of the first layer, of glycerin; and
    b. after the first layer is applied to human skin, apply on top of the first layer a powder layer comprising from about 10% to about 30%, by weight of the powder layer, of substantially spherical particles selected from the group consisting of coated starch, uncoated starch, coated starch derivatives, uncoated starch derivatives, coated crosslinked starch, uncoated crosslink starch, silicone elastomer particles, and combinations thereof, wherein the powder layer includes less than 0.5% pigment and is an oil-in-water emulsion comprising a non-volatile oil present in a concentration level such that the weight ratio of non-volatile oil to spherical particulate material is from about 1:4 to about 1:1.

2. The method of claim 1, wherein at least one of, or both the first layer and the powder layer have a contrast ratio of less than about 20.

3. The method of claim 1, wherein the first layer comprises from about 2% to about 25%, by weight of the first layer, other humectants.

4. The method of claim 1, wherein the powder layer comprises less than about 4%, by weight of the powder layer of mica, talc, and other substantially non-spherical particles.

5. The method of claim 1, wherein the first layer comprises from about 1%, by weight of the first layer, of skin care actives selected from the group consisting of sugar amines, vitamins, oil control agents, photosterols, hexamidine compounds, tightening agents, anti-wrinkle actives, anti-atrophy actives, flavonoids, N-acyl amino acid compounds, retinoids, peptides, anti-cellulite agents, desquamation actives, anti-acne actives, anti-oxidants, radical scavengers, anti-inflammatory agents, tanning actives, skin lightening agents, botanical extracts, antimicrobial actives, antifungal actives, antibacterial actives, sensates, and combinations thereof.

6. The method of claim 1, wherein the particles in the powder layer have an average diameter of from about 1 μm to about 40 pm.

7. The method of claim 1, wherein there is one or more middle layers applied over the first layer and before the powder layer, the middle layers comprising a skin care composition.

8. The method of claim 1, wherein the powder layer comprises less than about 10% by weight of the powder layer of humectant.

9. The method of claim 1, wherein the first layer is water based and is in the form of an aqueous solution, aqueous gel, aqueous dispersion, oil-in-water emulsion, or a water-in-oil-in-water emulsion.

10. The method of claim 1, wherein the non-volatile oil of the powder layer is at least 70% silicone oil.

11. The method of claim 10, wherein the silicone oil of the powder layer is dimethicone.

\* \* \* \* \*